United States Patent [19]

Hoekwater et al.

[11] Patent Number: 5,356,380
[45] Date of Patent: Oct. 18, 1994

[54] DRUG DELIVERY SYSTEM

[75] Inventors: Mark Hoekwater, Vernon Hills; Jeffrey S. Nordquist, Barrington; Thomas A. Fowles, McHenry, all of Ill.; James Sertic, Kalamazoo, Mich.; Brian J. Gorman, Lake Geneva, Wis.

[73] Assignee: Baxter International Inc., Deerfield, Ill.

[21] Appl. No.: 780,604

[22] Filed: Oct. 23, 1991

[51] Int. Cl.⁵ .................................... A61M 37/00
[52] U.S. Cl. .................................... 604/85; 604/88; 604/244; 604/412; 604/905; 285/4; 285/921
[58] Field of Search ............ 604/82, 83, 85, 88, 604/91, 92, 111, 244, 411–414, 905; 285/4, 921

[56] References Cited

U.S. PATENT DOCUMENTS

| | | | |
|---|---|---|---|
| 3,866,950 | 2/1975 | Skoch et al. | 285/4 |
| 3,938,518 | 2/1976 | Tischlinger | 604/413 |
| 3,977,555 | 8/1976 | Larson | 604/411 |
| 4,304,422 | 12/1981 | Schwarz | 285/4 |
| 4,392,850 | 7/1983 | Elias et al. | 604/82 |
| 4,568,346 | 2/1986 | van Dijk | 604/414 |
| 4,757,916 | 7/1988 | Goncalves | 222/83 |
| 4,804,366 | 2/1989 | Zbed et al. | 604/85 |
| 4,805,932 | 2/1989 | Imhof et al. | 285/4 |
| 4,850,978 | 7/1989 | Dudar et al. | 604/201 |
| 4,898,209 | 2/1990 | Zbed | 137/614.04 |
| 4,927,423 | 5/1990 | Malmborg | 604/88 |
| 4,936,841 | 6/1990 | Aoki et al. | 604/413 |
| 5,049,129 | 9/1991 | Zbed et al. | 604/85 |
| 5,167,642 | 12/1992 | Fowes | 604/263 |
| 5,171,214 | 12/1992 | Kolber et al. | 604/82 |

Primary Examiner—C. Fred Rosenbaum
Assistant Examiner—Mark O. Polutta
Attorney, Agent, or Firm—Paul E. Schaafsma; Amy L. H. Rockwell; Paul C. Flattery

[57] ABSTRACT

A drug delivery device is provided comprising a cartridge body including an upper portion defining a vial receiving area and terminating in a wall, the cartridge body including a cannula extending from the wall. A vial including a beneficial agent is coupled by a retaining member to the cartridge body in an inactivated position. The retaining member allows the vial to move to an activated position. The retaining member including an outer member and an inner member, the inner member separating from portions of the outer member as the vial moves from the inactivated position to the activated position.

20 Claims, 1 Drawing Sheet

DRUG DELIVERY SYSTEM

BACKGROUND OF THE INVENTION

The present invention relates generally to the delivery of a beneficial agent to a patient or into a system for later delivery to a patient. More specifically, the present invention relates to an improved drug delivery system.

For many applications, drugs can be mixed with a diluent before being delivered, for example, intravenously, to a patient. The diluent can be, for example, a dextrose solution, a saline solution, or even water. To this end, many such drugs are supplied in powder form and packaged in glass vials or ampules. Other drugs, such as some chemotherapy drugs, are packaged in glass vials or ampules in a liquid state.

Powder drugs can be reconstituted by utilizing a syringe to inject liquid into a vial for mixing; the syringe eventually withdrawing the mixed solution from the vial. When a drug must be diluted before delivery to a patient, the drug is often injected into a container of diluent after it is reconstituted; the container can be connected to an administration set for delivery to the patient.

Drugs may be packaged separately from the diluent for various reasons. One of the most important reasons is that many drugs do not retain their chemical and physical stability when mixed with a diluent and thus cannot be stored for any substantial period of time. Also, drugs are often packaged separately from the diluent because many companies that manufacture drugs are not engaged in the business of providing medical fluids in containers for intravenous delivery, and vice versa.

Therefore, a doctor, nurse, pharmacist or other medical personnel must mix the drug and diluent. This presents a number of problems. The reconstitution procedure is time consuming and requires aseptic technique. The operator must provide the proper diluent and a syringe before beginning. Often the powdered drug is "caked" at the bottom of the vial. Thus, when liquid is injected into the vial from a syringe the surface area of contact between the liquid and the powdered drug may be quite small initially, thus making the mixing procedure even more time consuming.

Because of the limited vial volume, increasing the drug concentration in the diluent makes it harder to complete the reconstitution process. The operator may attempt to solve this problem by repeatedly injecting solution into the vial, mixing and withdrawing the solution. But, this attempt to solve the problem makes additional injections and movement of the syringe necessary, increasing the likelihood of contamination. Also, it is sometimes difficult to remove all of the drug and/or liquid from the vial, thus increasing the time required to perform the reconstitution procedure.

The reconstitution procedure should be performed under preferably sterile conditions. This requirement requires the operator to be more cautious, thereby consuming more time. Additionally, sterile conditions are often hard to maintain. In some instances, a laminar flow hood may be required under which the reconstitution procedure is performed.

A further concern is that some drugs, such as some chemotherapy drugs, are toxic. Exposure of the operator to the drugs during reconstitution can be dangerous, especially if the operator works with such drugs on a daily basis and is repeatedly exposed to them.

After a drug is reconstituted and withdrawn into a syringe barrel, the drug can, in some instances, be immediately injected into the patient. More typically, however, the reconstituted drug is injected from the syringe into a larger container of solution for connection to an intravenous administration set. A larger container of solution may be necessary because often the reconstituted drug in the syringe is at such a concentration as to cause local toxicity in the veins of a patient near the injection site where the needle pierces the skin. This can create severe vein irritation which can be harmful.

Additionally, even though the proper dose of medication may be in the syringe, immediate injection into the patient's blood stream can create a condition of systemic toxicity wherein the level of drug concentration in the patient's entire blood stream is dangerously high. Yet another reason for not making an injection from the syringe directly into the patient is that such an injection creates an additional injection site into the patient; this can be painful for the patient and provides another opportunity for infection.

For these reasons, the reconstituted drug is more typically injected into a diluent container.

There are a variety of examples of drug delivery systems that can be used to deliver drugs to a patient and/or reconstitute a drug. An example of such a system is disclosed in U.S. Pat. No. 4,850,978. The system includes a cartridge for introducing a beneficial agent into a fluid conduit for delivery of the agent to a patient. The cartridge includes a rigid hollow tube and an agent-containing chamber slidably mounted at least partially within the hollow tube. In a first, pre-use position, the chamber extends farther from the hollow tube than it does in a second position. A cannula is mounted to the hollow tube extending opposite the chamber. When the chamber is in the second position, the cannula pierces the closure means creating a fluid flow path.

U.S. Pat. No. 4,804,366 also discloses a drug delivery system including an adapter having an improved flow path means providing both an inlet and an outlet to the agent-containing chamber of a cartridge. The cartridge and adapter permit a single opening through the injection sites at opposite ends of the flow path means, while still permitting simultaneous flow both into and out of the chamber. An adapter and a cartridge is provided, including a rigid cannula with an inlet and an outlet and a shell substantially coaxial with and spaced from the cannula intermediate of the cannula inlet and the cannula outlet, so that the shell of the cannula define a channel therebetween. Both the cannula inlet and the cannula outlet are adaptable to form a single piercing opening in a resilient injection site associated with the receptacle of the delivery system. Both the channel outlet and cannula inlet are adapted to form a single piercing opening in a resilient injection site associated with the cartridge.

SUMMARY OF THE INVENTION

The present invention provides an improved drug delivery system. The system allows the delivery of a medicament from a drug vial directly into an intravenous (IV) line to a patient. The system provides means for ensuring that the drug vial is retained in an inactivated, uncompromised position until the drug is to be delivered. At that time, the system, and specifically the vial, is easily activated by a nurse, pharmacist, or physician. Once so activated, the system allows the drug to be administered to a patient.

The system provides many advantages. The system is designed so that it will accommodate multiple sized drug vials. Specifically, it will incorporate drug vials that have crimp (opening) diameters smaller than the vial body diameters.

The system additionally provides means for allowing the user to easily determine when the drug vial has been completely activated into the cartridge.

Moreover, the system provides a tamper evident feature that alerts medical personnel that the vial has been, or may have been, activated.

Furthermore, the system allows the cannula, when the system is activated, to be located near the bottom of the vial containing the drug. This insures that even drug that is caked-on the bottom of the vial will be reconstituted. Even though the system allows the cannula, when the system is activated, to be located near the bottom of the vial, it still allows the vial to be flush with the remaining portions of the cartridge when so activated.

To this end, the present invention provides, in an embodiment, a cartridge for introducing a beneficial agent into a fluid conduit for delivery of the beneficial agent to a patient. The cartridge comprises a hollow tube and a chamber having a beneficial agent therein. The chamber is coupled to a first end of the hollow tube and slidably mounted at least partially within the hollow tube from a first position to a second position, such that in the first position the chamber extends a greater distance from the hollow tube than in the second position. A cannula is mounted within the hollow tube and a frangible retaining member is coupled to a top portion of the hollow tube. The frangible retaining member secures the chamber to the hollow tube. The frangible retaining member includes first and second parts for securing the chamber in the first position and includes means for causing the second part to separate from the first part allowing the chamber to move to the second position.

In an embodiment, the first part includes means for coupling the frangible retaining member to the hollow tube and the first part of the retaining member remains secured to the hollow tube after the second part separates from the first part.

In an embodiment, the second part of the frangible retaining member includes an upper and lower portion, the upper portion having means for retaining at least a portion of the chamber therein, the upper and lower portion being divided by a wall including an aperture for receiving the cannula.

In an embodiment, the second part of the frangible retaining member defines an area for receiving a portion of the chamber and includes means for securing the portion of the chamber therein. The means for securing can be a flange circumscribing at least a portion of an interior of the second part.

In an embodiment, the present invention provides a drug delivery device comprising a cartridge body including an upper portion defining a vial receiving area, the upper portion terminating in a wall with a cannula extending from the wall. A vial is provided including a beneficial agent. A retaining member for coupling the vial to the upper portion is secured to an end of the upper portion and allows the vial to remain in an inactivated position and to move to an activated position. The retaining member including an outer member and an inner member, the inner member separating from portions of the outer member as the vial moves from the inactivated position to the activated position.

In an embodiment, the inner member of the retaining member includes an upper portion and a lower portion, the upper portion receiving at least a part of the vial. The wall of the upper portion of the cartridge body can include means for receiving a part of the lower portion of the inner member of the retaining member when the vial is in the activated position.

In an embodiment, an outer wall of the upper portion of the cartridge body includes a flange circumscribing an end thereof and the outer member of the retaining member includes a skirt defining a groove for receiving the flange and thereby securing the outer member to the upper portion.

In a further embodiment, a drug vial retaining member for coupling a vial to a drug delivery cartridge body, including a cannula disposed therein, is provided. The retaining member comprising a first outer member for securing the retaining member to an end of the cartridge body and a second inner member defining an interior for receiving at least a part of the drug vial. The second inner member being secured to the first outer member by frangible members. The retaining member is so constructed and arranged that the retaining member secures the vial in a first inactivated position until the second inner member is separated from the first outer member.

Additionally, the present invention provides a method for reconstituting a drug comprising the steps of: providing a cartridge body that includes a cannula; coupling a retaining member having a first part and a second part to an end of the cartridge; securing a vial including a drug to the end of the cartridge by inserting at least a portion of the vial into an interior of the retaining member; and causing the second part of the retaining member to separate from the first part of the retaining member and the cannula to enter the vial.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an improved drug delivery device. The drug delivery device providing means for maintaining the device, and specifically a vial coupled thereto in a first, inactivated position until it is desired to deliver the medicament in the vial to a patient.

Figure 1:
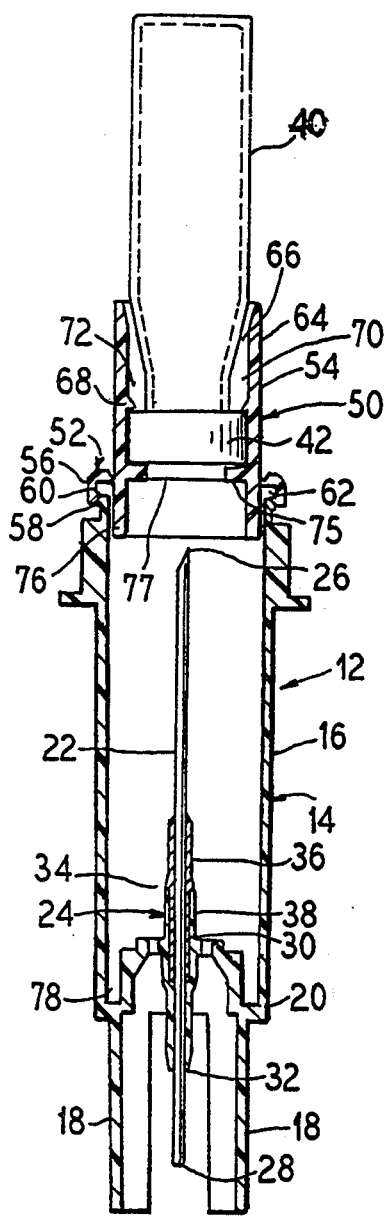
FIG. 1 illustrates a cross-sectional perspective view of an embodiment of the drug delivery device of the present invention in a first, inactivated position.

Referring now to FIG. 1, there is illustrated an inline device, or cartridge, that is to be coupled to an IV set.

The cartridge, in some respects, is similar to that disclosed in U.S. Pat. No. 4,804,366, the disclosure of which is incorporated herein by reference. Briefly, the cartridge 12 includes an adapter 14 having a rigid hollow cylinder or tube means 16 and a keyway wall 18, with the keyway wall 18 being part of the tube 16. The keyway wall 18 includes snaps 19 which assist in containing the cartridge 12 on the IV set. A plate 20 is mounted across the tube 14 and defines the starting point for the keyway wall 18.

A cannula 22 extends through the plate 20. A generally cylindrical shell 24 extends from both sides of the plate 20. The hollow tube 16, the plate 20, the keyway wall 18, and the shell 24 may all be formed as a single piece of the same material such as a plastic.

The shell 24 is spaced from the cannula 22 with the shell 24 encompassing the cannula 22 but being shorter than either end of the cannula 22. The cannula 22 includes an inlet 26 and an outlet 28. The inlet 26 preferably is pointed to facilitate piercing. The outlet 28 can also be pointed but can be, in an embodiment such as that depicted in FIG. 2, blunt. Likewise, if desired, the outlet can be covered by a sheath (not shown). In this regard, reference is made to U.S. patent application Ser. No. 07/573,529, filed on Aug. 27, 1990, and entitled: "SHEATH FOR CANNULA", the disclosure of which is hereby incorporated by reference.

The shell 24 is intermediate of the cannula inlet and outlet 26 and 28, respectively. The cannula 22 and the shell 24 define a channel 30 therebetween. In a preferred embodiment, the periphery of the cannula 22 is circular along its length. Similarly, the internal surface of the shell 24 is preferably arcuate and preferably circular along its length.

The channel 30 includes a channel 32 inlet defined between the shell 24 and the cannula 22, short of the cannula outlet 28. Similarly, the channel 30 includes a channel outlet 34 defined by the shell 24 and the plastic cannula holder 36, short of the cannula inlet 26.

A preferably plastic cannula holder 36 is secured to the cannula 22. The cannula holder 36 grips the cannula 22. Extension means 38 extend between the cannula holder 36 and the shell 24, across the channel 30, thereby securing the cannula 22 relative to the shell 24. In the illustrated embodiment, the extension means 38 is part of the holder 36.

The cannula 22 is secured to the shell 24 while still maintaining an open flow path through the channel inlet 32, the channel 30, and the channel outlet 34. Thus, a very small flow path is created outside a single cannula 22, with precision.

As discussed in more detail below, the cartridge 12 further includes, or is coupled to, a tubular chamber or vial 40 containing a beneficial agent such as a dry powdered drug, although the agent may also be a liquid. In an embodiment, the tubular chamber 40 is a glass vial. A pierceable stopper 42 or other closure means closes the tubular chamber 40.

The shell 24, along with the channel outlet 34 and the cannula inlet 26, are designed to pierce the pierceable stopper 42 or other injection site/closure means to enter the vial 40 having the beneficial agent therein. Similarly, the shell 24 along with the defined channel inlet 32, together with the cannula outlet 28, are designed to pierce the injection site in a receptacle.

The pierceable stopper 42 is mounted within the mouth of the vial 40. The pierceable stopper 42 can be secured within the vial 40 by means of a metal band about the periphery of the mouth and the rubber stopper, in a known manner for securing a stopper in a standard drug vial. The vial 40 is slidably mounted within the rigid cylinder such that the rubber stopper 42 faces the plate 20. In place of the pierceable stopper 42, other pierceable closure means can be provided.

To couple the vial 40 to an end of the tube 16, a frangible retaining member 50 is provided. Pursuant to the present invention, the frangible retaining member 50 allows the vial 40 to be coupled to the tube 16 in a first inactivated position, illustrated in FIG. 1. As discussed in more detail below, when it is desired to access the drug or beneficial agent contained within the vial 40, the frangible retaining member 50 allows the vial 40 to be moved to a second activated position, illustrated in FIG. 2.

Figure 2:
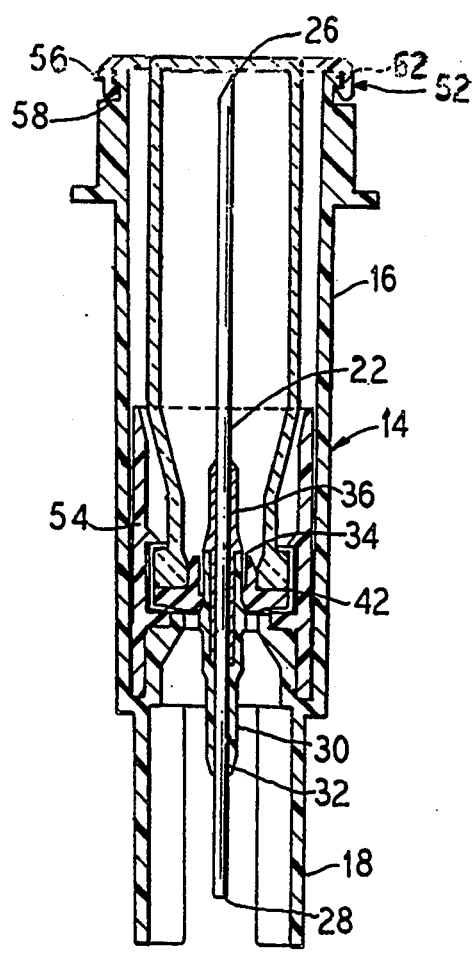
FIG. 2 illustrates a cross-sectional perspective view of the drug delivery device of FIG. 1 in a second, activated position.
Figure 3:
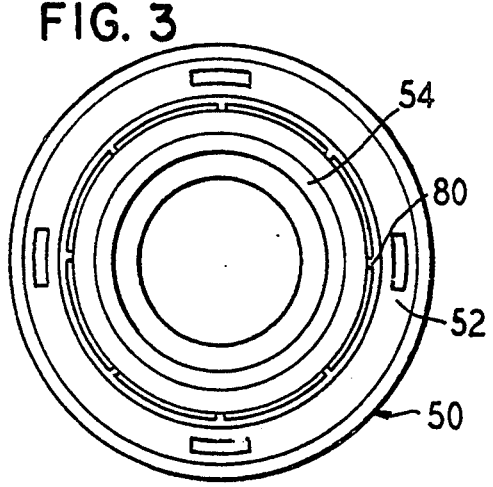
FIG. 3 illustrates a top elevational view of an embodiment of the retaining member of the present invention.

Referring now to FIGS. 1–3, the frangible retaining member 50 includes a first outer portion 52 that is secured to a second inner portion 54. The first outer portion 52 defines a retaining ring and is designed to secure the frangible retaining member 50 to the end of the tube 16. To this end, the first outer portion 52 includes an extending skirt 56 including a flange 58 extending inwardly therefrom. The extending skirt 56 and flange 58 define a groove 60. The groove 60 is designed to receive a flange 62 that circumscribes an end of the tube 16.

Preferably, the flange 62 of the tube 16 is beveled. Likewise, preferably, the flange 58 on the skirt 56 is beveled allowing the skirt portion 56 to snap on to the tube 16 securing the flange 62 within the groove 60 defined thereby. This securely couples the frangible retaining member 50, and specifically the first outer portion 52, to the tube 16.

In the embodiment illustrated in FIGS. 1–3, the second inner portion 54 includes wall members 64 that define an interior 66 extending from the first outer portion 52. The interior 66 defined thereby is designed to receive, as illustrated in FIG. 1, the vial 40.

In the embodiment illustrated, the interior 66 of the second inner portion 54 includes a flange 68 circumscribing the interior walls 70 thereof. The flange 68 is designed, as illustrated, to securely receive the vial 40 therein, locking the vial in place. To this end, the flange 68 includes beveled walls 72 allowing the vial 40 to be pushed downwardly within the interior 66 of the second outer member 54 snapping the vial 40, and specifically, a cap portion thereof, into a bottom portion 74 of the interior 66.

Figure 4:
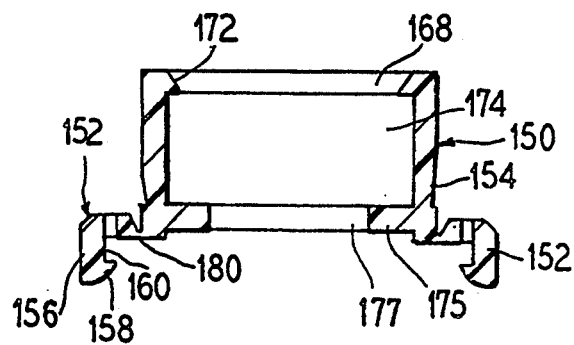
FIG. 4 illustrates a cross-sectional view of a further embodiment of the retaining member of the present invention.

In the embodiment, illustrated, the second inner member 54 also includes wall members 76 extending downwardly from the first outer portion 52. These walls 76 are designed to mate with grooves 78 located in the wall 20 in the cartridge body. Of course, as illustrated in FIG. 4, if desired, these wall members 76 are not necessary, but, afford the user a visible sign of when the vial 40 has been activated.

The interior 66 of the second inner portion 54 also includes a wall member 75. The wall member 75 provides a member against which the vial 40 can rest. The wall member 75 includes an aperture 77 for allowing the cannula 22 to pierce the vial 40.

As previously stated, the first and second members 52 and 54 are secured together so as to be frangible. To this end, as illustrated in FIG. 3 specifically, the first and second members are secured together by frangible members 80.

As illustrated in FIG. 1, when the first and second members 52 and 54 have not been broken apart, the vial 40 is in a first inactivated position. Referring now to FIG. 2, when it is desired to activate the vial, i.e., allow the cannula to pierce the vial 40, this is achieved by breaking the frangible retaining members 80 securing the first and second members 52 and 54 together. Once the first and second members 52 and 54 are separated from each other, the first member 52 remains secured to the end of the tube 16 and the second member 54 travels with the vial 40 within the interior of the tube.

Because the first and second members 52 and 54 must be separated prior to activation of the vial 40, the present invention not only provides a method for securely coupling the vial to the tube 16, but additionally provides a tamper evident construction. It will be readily apparent to the user of the product if the vial 40 has been activated or there was an attempt to activate the vial 40.

When the chamber 40 is in a first position, the rubber stopper 42 has not been pierced by either the shell 24 or the cannula inlet 26. The pierceable stopper 42 remains spaced from the cannula 22 when the cartridge 40 is in the first position.

When it is desired to access the vial 40, the operator then grasps the rigid tube 16 and pushes down on the top of the chamber 40 with, for example, the thumb. This causes the frangible members 80 to break allowing the first and second members 52 and 54 to separate. This thereby allows the chamber 40 to slide downwardly within the hollow tube 16.

In this one action, first the cannula inlet 26 and then the shell 24 pierce the pierceable stopper 42. In the preferred construction illustrated in the drawings, after the cannula inlet 26 pierces the stopper 42, the cannula holder 36 pierces the stopper, followed by the shell 24, with the shell and the cannula holder defining the channel outlet 34, which is now disposed slightly within the chamber 40. In the same motion, the chamber 40 continues to be urged into the hollow tube 16 until the lower portion of the retaining member 50 is received within the grooves defined by the wall 20 of the tube 16.

The system allows one to vary the resultant location of the cannula inlet 26 with respect to the vial bottom. In many applications wherein a drug is to be reconstituted, it may be desirable to locate the cannula inlet 26 near the bottom of the vial to ensure that drug does not remain caked-on. As illustrated in FIG. 2, when activated, the system allows the cannula inlet 26 to be located in juxtaposition to the vial bottom and allows the vial to still remain flush with remaining portions of the cartridge.

Preferably, a vial cover (not shown) is provided such as the vial cover illustrated and disclosed in U.S. Pat. No. 4,804,366. The vial cover will hold the drug vial is a straight fashion with respect to the cartridge and so that the frangibles will not be cantilevered and broken prior to activation.

Referring now to FIG. 4, an embodiment of the retaining member 150 of the present invention is illustrated. In the illustrated embodiment, wall member 154 terminates in flange member 168. It has been found that this provides a structure that will secure the vial 40, but reduces material and thereby costs. Similarly, the retaining member does not include the wall member 76 extending downwardly as illustrated in the embodiment of the invention illustrates in FIGS. 1 and 2. This feature likewise reduces costs.

In all other aspects, the retaining member 150 is similar to retaining member 50 illustrated in FIGS. 1-3. In this regard, the retaining member 150 includes an interior portion 174 for receiving the cap portion of the vial. A wall 175 is provided having an aperture 177. An outer portion 152 is provided having an extending skirt 156 and flange 158 defining a groove 160. The retaining member 150 functions similarly to retaining member 50.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A cartridge for introducing a beneficial agent into a fluid conduit for delivery of the beneficial agent to a patient comprising:
   a hollow tube having a cannula holder;
   a chamber having a beneficial agent therein, the chamber being coupled by a frangible retaining member to a first end of the hollow tube, the chamber being slidably mounted at least partially within the hollow tube from a first position to a second position, such that in the first position, the chamber extends a greater distance from the hollow tube than in the second position;
   a cannula mounted within the cannula holder at a second end substantially opposite the first end of the hollow tube; and
   the frangible retaining member being coupled to the first end of the hollow tube and including a first part and a second part for securing the chamber in the first position, and including means for allowing the second part to separate from the first part allowing the chamber to move to the second position.

2. The cartridge of claim 1 wherein the first part includes means for securing the frangible retaining member to the hollow tube and the first part remains secured to the hollow tube after the second part separates from the first part.

3. The cartridge of claim 1 wherein the second part of the frangible retaining member includes an elongated portion for securely receiving at least a portion of the chamber therein.

4. The cartridge of claim 1 wherein the second part of the frangible retaining member includes an upper portion and a lower portion, the upper portion having means for retaining at least a part of the chamber therein, the upper portion and lower portion being divided by a wall including an aperture for receiving the cannula.

5. The cartridge of claim 1 wherein the second part of the frangible member defines an interior area for receiving a portion of the chamber and includes means for securing the portion of the chamber within the interior area.

6. The cartridge of claim 5 wherein the means for securing is a flange circumscribing at least a portion of the interior of the second part.

7. The cartridge of claim 6 wherein the flange includes a beveled portion.

8. The cartridge of claim 1 wherein the means for allowing the second part to separate from the first part includes at least one frangible retaining member securing the first part to the second part.

9. A drug delivery device comprising:

a cartridge body including an upper portion defining a vial receiving area and terminating in a wall, the cartridge body including a cannula having opposite ends extending through the wall in respective opposite directions from the wall;

a vial including a beneficial agent; and a retaining member for coupling the vial to the cartridge body and maintaining the vial in an inactivated position and for allowing the vial to move to an activated position by one end of the cannula penetrating into the vial, the retaining member including an outer member and an inner member, the inner member separating from the outer member as the vial moves from the inactivated position to the activated position.

10. The drug delivery device of claim 9 wherein the inner member of the retaining member includes an upper portion and a lower portion, the upper portion defining an interior for receiving at least a part of the vial.

11. The drug delivery device of claim 9 wherein the wall of the cartridge body includes means for receiving a part of the lower portion of the retaining member when the vial is in the activated position.

12. The drug delivery device of claim 9 wherein the upper portion of the inner member of the retaining member includes means for securing the vial in the interior.

13. The cartridge of claim 12 wherein the means for securing is a flange circumscribing at least a portion of a wall of the inner member that defines the interior.

14. The drug delivery device of claim 9 wherein the cartridge body includes a flange circumscribing an end thereof and the outer member of the retaining member defines a groove for receiving the flange securing the outer member to the cartridge body.

15. The drug delivery device of claim 9 wherein the inner member is coupled to the outer member by at least one frangible retaining member.

16. A method for reconstituting a drug comprising:

providing a cartridge body that includes a cannula holder for holding a cannula for penetrating a vial including a drug;

coupling a retaining member having a first part and a second part to an end of the cartridge body;

securing the vial including the drug to the end of the cartridge body by inserting at least a portion of the vial into an interior of the retaining member; and causing the second part of the retaining member to separate from the first part of the retaining member and the cannula to enter the vial.

17. The method of claim 16 including the step of providing in the interior of the retaining member with means for securing the vial therein.

18. The method of claim 18 including the step of causing a portion of the second part of the retaining member to enter a space defined by an interior portion of the cartridge body when the cannula has fully entered the vial.

19. The method of claim 16 including the step of securing the retaining member to the cartridge body by causing a flange circumscribing an outer wall of the cartridge body to enter a groove defined by the first part of the retaining member.

20. The method of claim 16 including the step of securing the vial within the retaining member by providing a flange that circumscribes an interior of the retaining member.

* * * * *